United States Patent
Wang et al.

(10) Patent No.: US 8,961,862 B2
(45) Date of Patent: *Feb. 24, 2015

(54) METHOD OF IMPROVING FRACTURE TOUGHNESS OF IMPLANTABLE MEDICAL DEVICES THROUGH ANNEALING

(71) Applicant: Abbott Cardiovascular Systems Inc., Santa Clara, CA (US)

(72) Inventors: Yunbing Wang, Sunnyvale, CA (US); James Oberhauser, Saratoga, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/794,537

(22) Filed: Mar. 11, 2013

(65) Prior Publication Data

US 2013/0207314 A1    Aug. 15, 2013

Related U.S. Application Data (63) Continuation of application No. 12/189,620, filed on Aug. 11, 2008, now Pat. No. 8,394,317.

(51) Int. Cl.
| | |
|---|---|
| *B29C 49/00* | (2006.01) |
| *B29C 49/64* | (2006.01) |
| *B29C 51/00* | (2006.01) |
| *A61L 31/06* | (2006.01) |
| *A61L 31/14* | (2006.01) |

(52) U.S. Cl.
CPC ............... *B29C 51/002* (2013.01); *A61L 31/06* (2013.01); *A61L 31/14* (2013.01)
USPC ............ 264/573; 264/534; 264/535; 264/346

(58) Field of Classification Search
USPC ....... 264/171.26, 178 R, 209.1, 209.3, 209.4, 264/209.5, 211, 211.13, 235, 346, 514, 515, 264/523, 534, 540, 563, 564, 567
See application file for complete search history.

(56) References Cited

U.S. PATENT DOCUMENTS

| | | | |
|---|---|---|---|
| 5,211,902 | A | 5/1993 | Unger et al. |
| 6,319,576 | B1 | 11/2001 | Rule et al. |

(Continued)

FOREIGN PATENT DOCUMENTS

| | | |
|---|---|---|
| EP | 1 872 808 | 1/2008 |
| JP | 2006-519672 | 8/2006 |

(Continued)

OTHER PUBLICATIONS

International Search Report for PCT/US2009/053182, mailed Nov. 9, 2009, 7 pgs.

(Continued)

*Primary Examiner* — Ryan Ochylski
(74) *Attorney, Agent, or Firm* — Squire Patton Boggs (US) LLP (57) ABSTRACT

Methods of fabricating a polymeric implantable device with improved fracture toughness through annealing are disclosed herein. A polymeric construct is annealed with no or substantially no crystal growth to increase nucleation density. After the annealing, crystallites are grown around the formed nuclei. An implantable medical device, such as a stent, can be fabricated from the polymer construct after the crystallite growth.

12 Claims, 4 Drawing Sheets

(56) References Cited

U.S. PATENT DOCUMENTS

| | | | |
|---|---|---|---|
| 6,932,930 | B2 | 8/2005 | DeSimone et al. |
| 8,337,739 | B2 * | 12/2012 | Wang et al. .................. 264/294 |
| 8,372,332 | B2 * | 2/2013 | Wang et al. .................. 264/564 |
| 8,394,317 | B2 * | 3/2013 | Wang et al. .................. 264/573 |
| 8,535,593 | B2 * | 9/2013 | Wang et al. .................. 264/346 |
| 2003/0083732 | A1 | 5/2003 | Stinson |
| 2004/0181271 | A1 | 9/2004 | Desimone et al. |
| 2006/0246108 | A1 | 11/2006 | Pacetti et al. |
| 2007/0038290 | A1 | 2/2007 | Huang et al. |
| 2007/0132156 | A1 | 6/2007 | Burgermeister et al. |
| 2007/0200271 | A1 | 8/2007 | Dave |
| 2007/0253996 | A1 | 11/2007 | Bin et al. |
| 2007/0253999 | A1 | 11/2007 | Huang et al. |
| 2007/0283552 | A1 | 12/2007 | Gale et al. |
| 2008/0014240 | A1 | 1/2008 | Gale et al. |
| 2008/0051873 | A1 | 2/2008 | Cottone et al. |
| 2008/0177374 | A1 | 7/2008 | Zheng et al. |
| 2009/0248147 | A1 | 10/2009 | Wang |
| 2010/0025894 | A1 | 2/2010 | Kleiner et al. |

FOREIGN PATENT DOCUMENTS

| | | |
|---|---|---|
| WO | WO 2004/080332 | 9/2004 |
| WO | WO 2007/142736 | 12/2007 |
| WO | WO 2008/008495 | 1/2008 |
| WO | WO 2010/017090 | 2/2010 |
| WO | WO 2010/019478 | 2/2010 |

OTHER PUBLICATIONS

International Search Report for PCT/US2010/034077, mailed Jan. 20, 2011, 6 pgs.

International Search Report for PCT/US2009/053029, mailed Aug. 12, 2010, 8 pgs.

Anderson et al., "Melt preparation and nucleation efficiency of polylactide stereocomplex crystallites", Polymer 47, pp. 2030-2035 (2006).

Borokhovskii et al., "Thermodynamic analysis of nucleus formation in crystallization of polymers", Vysokomol. Soyed. A18, No. 11, pp. 2406-2411 (1976).

Brizzolara et al., "Mechanism of the Stereocomplex Formation between Enantiomeric Poly(lactide)s", Macromolecules, vol. 29, pp. 191-197 (1996).

Kawamoto et al., "Nucleating-Agent for Poly(L-lactic acid)—An Optimization of Chemical Structure of Hydrazide Compound for Advanced Nucleation Ability", J. of Applied Polymer Science, vol. 103, pp. 198-203 (2007).

Krouse et al., "Stereocomplex Formation between Enantiomeric Poly(lactides)", Macromolecules, vol. 20, pp. 904-906 (1987).

Schmidt et al., "Polylactide stereocomplex crystallites as nucleating agents for isotactic polylactide", J. of Pol. Science vol. 39, pp. 300-313 (2001).

Takasaki et al., "Development of Stereocomplex Crystal of Polylactide in High-Speed Melt Spinning and Subsequent Drawing and Annealing Processes", Journal of Macromolecular Science: Part B—Physics, vol. B42, Nos. 3 & 4, pp. 403-420 (2003).

Tsuji et al., "In vitro hydrolysis of blends from enantiomeric poly(lactide)s. Part 4: well-homo-crystallized blend and nonblended films", Biomaterials, vol. 24, pp. 537-547 (2003).

Tsuji et al., "Stereocomplex Formation between Enantiomeric Poly(lactic acid)s. 2. Stereocomplex Formation in Concentrated Solutions", Macromolecules, vol. 24, pp. 2719-2724 (1991).

Urayama et al., "Controlled crystal nucleation in the melt-crystallization of poly(L-lactide) and poly(L-lactide)/poly(D-lactide) stereocomplex", Polymer, vol. 44, pp. 5635-5641 (2003).

Van Vlack, "Elements of Materials Science and Engineering", Addison-Wesley Pub. Co., pp. 270-271. (1989).

Yash Khanna, "Rheological Mechanism and Overview of Nucleated Crystallization Kinetics", macromolecules, vol. 26, pp. 3639-3643 (1993).

A Notice of Reason for Rejection from JPO, dated May 27, 2014, for Appl. No. JP2012-510882, 2 pgs.

The translation of the Notice of Reason for Rejection from JPO, dated May 27, 2014, for Appl. No. JP2012-510882, 2 pgs.

Goto et al., "Effect of annealing on deformation and fracture behavior of injection molded PLA", J. of the Japanese Soc. For Strength and Fracture of Materials, vol. 42, No. 1, pp. 7-10 (2008).

Takahashi et al., "Effect of annealing on fracture behavior of injection molded PLA", Molding Process, vol. 19, pp. 21-22 (2008).

The translation of Takahashi et al., "Effect of annealing on fracture behavior of injection molded PLA", Molding Process, vol. 19, pp. 21-22 (2008).

Goto et al., "Influence of heat-treatment on mechanics characteristic and structure of PLA", Reports of Yamagata Research Institute of Technology No. 37, pp. 83-88 (2005).

The translation of Goto et al., "Influence of heat-treatment on mechanics characteristic and structure of PLA", Reports of Yamagata Research Institute of Technology No. 37, pp. 83-88 (2005).

* cited by examiner

METHOD OF IMPROVING FRACTURE TOUGHNESS OF IMPLANTABLE MEDICAL DEVICES THROUGH ANNEALING

BACKGROUND OF THE INVENTION

1. Field of the Invention

This invention relates to methods of manufacturing polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating the device in whole or in part from materials that erode or disintegrate through exposure to conditions within the body. Thus, erodible portions of the device can disappear or substantially disappear from the implant region after the treatment regimen is completed. After the process of disintegration has been completed, no portion of the device, or an erodible portion of the device will remain. In some embodiments, very negligible traces or residue may be left behind. Stents fabricated from biodegradable, bioabsorbable, and/or bioerodable materials such as bioabsorbable polymers can be designed to completely erode only after the clinical need for them has ended.

However, there are potential shortcomings in the use of polymers as a material for implantable medical devices, such as stents. There is a need for a manufacturing process for a stent that addresses such shortcomings so that a polymeric stent can meet the clinical and mechanical requirements of a stent.

SUMMARY OF THE INVENTION

Various embodiments of the present invention include a method of making an implantable medical device comprising: annealing a polymer construct, the polymer construct being in a temperature range that allows nuclei formation within the polymer with no or substantially no growth of crystallite around the nuclei during a selected annealing time; growing crystallites around the nuclei after the annealing time to obtain a desired crystallinity in the polymer construct; and fabricating an implantable medical device from the construct after the crystallite growth.

Additional embodiments of the present invention include a method of making a stent comprising: annealing a polymeric tube, the polymeric tube being in a temperature range that allows nuclei formation within the polymer with no or substantially no growth of crystallite around the nuclei during a selected annealing time; growing crystallites around the nuclei after the annealing time to obtain a desired crystallinity; and fabricating a stent from the tube after the crystallite growth.

DETAILED DESCRIPTION OF THE INVENTION

Various embodiments of the present invention relate to manufacture of polymeric implantable medical devices. In particular, the embodiments include a step of annealing a polymer construct during manufacture to increase the fracture toughness of a device made from the construct. The methods described herein are generally applicable to any polymeric implantable medical device. In particular, the methods can be applied to tubular implantable medical devices such as self-expandable stents, balloon-expandable stents, and stent-grafts.

Figure 1:
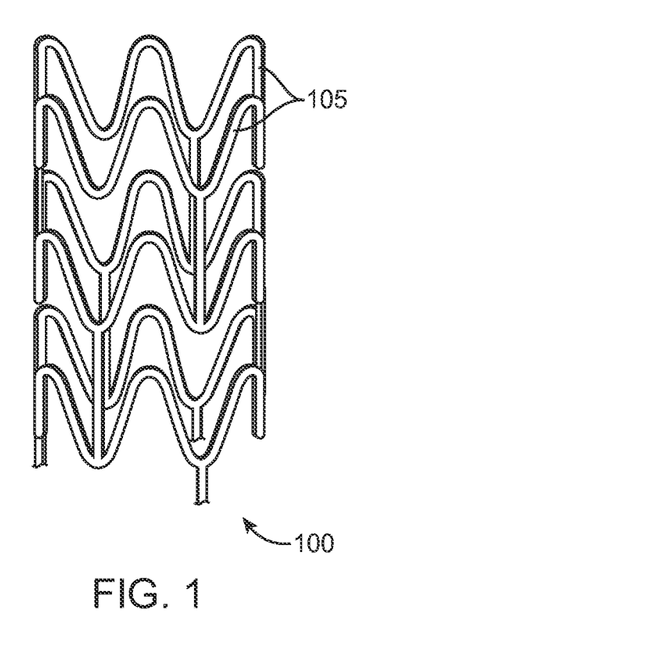
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from about a month to a few years. However, the duration is typically up to about six months, twelve months, eighteen months, or two years. In some situations, the treatment period can extend beyond two years.

As indicated above, a stent has certain mechanical requirements such as high radial strength, high modulus, and high fracture toughness. A stent that meets such requirements greatly facilitates the delivery, deployment, and treatment of a diseased vessel. With respect to radial strength, a stent must have sufficient radial strength to withstand structural loads, namely radial compressive forces, imposed on the stent as it supports the walls of a vessel. In addition, the stent must possess sufficient flexibility to allow for crimping, expansion, and cyclic loading. A polymeric stent with inadequete radial strength can result in mechanical failure or recoil inward after implantation into a vessel.

The strength to weight ratio of polymers is smaller than that of metals. To compensate for this, a polymeric stent can require significantly thicker struts than a metallic stent, which results in an undesirably large profile. One way of addressing the strength deficiency of polymers is to fabricate a stent from a deformed polymer construct. Deforming polymers tends to increase the strength along the direction of deformation. Thus, a stent fabrication process can include radially deforming a polymer tube and cutting a stent from the deformed tube.

With respect to toughness, a polymer stent should also have a high resistance to fracture. Semicrystalline polymers such as poly(L-lactide) (PLLA) that are suitable as stent materials tend to be brittle under biological conditions or conditions within a human body. Specifically, such polymers can have a glass transition temperature (Tg) above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

A number of strategies may be employed to improve the fracture toughness of semicrystalline polymers such as PLLA. For example, a rubbery phase (or toughening agent) may be incorporated in the rigid polymer, such as polycaprolactone or polytrimethylcarbonate through chemical reaction or physical blending. However, this results in decreased strength and modulus.

Alternatively, fracture toughness can be improved by reducing the size of the polymer crystals and increasing the density of the nuclei from which the crystals grow. Nucleation density can be increased through the addition of nucleating agents [e.g., ethylenebis(12-hydroxystearylamide), cyclohexanedicarboxylic dianilide, and tetramethylenedicarboxylic disalicyloyihydrazide]. However, the poor chemical compatibility between these small molecule nucleating agents and PLLA would engender poor mechanical properties.

Generally, in the crystallization of polymers, there are two separate events that occur. The first event is the formation of nuclei in the polymer matrix. The second event is growth of the crystallite around these nuclei. The overall rate of crystallization of the polymer is dependent, therefore, on the equilibrium concentration of nuclei in the polymer matrix, and on the rate of growth of crystallites around these nuclei.

Semicrystalline polymers can contain both amorphous and crystalline domains at temperatures below the melting point. Amorphous regions are those in which polymer chains are in relatively disordered configurations. Crystalline domains or crystallites are those in which polymer chains are in ordered configurations with segments of polymer chains essentially parallel to one another.

The classical view of polymer crystallization is a thermodynamically "frustrated" nucleation and growth process. The transition from the disordered rubber-like state where flexible chains adopt the random coil conformation to a rigid, ordered, three-dimensional state has been formally treated as a classical first-order transition. Crystallites form at the stable nuclei and grow by reorganizing random coil chains into chain-folded crystalline lamellae (ca. 10 nm thick). However, individual segments of polymer molecules are often unable to adopt the thermodynamically desirable conformation state necessary for crystallization before adjacent segments crystallize, locking in non-equilibrium amorphous structure. Thus, semicrystalline polymers form a mixture of ordered crystalline and disordered amorphous regions. The crystalline lamellae form sheaf-like stacks a few lamellae thick (~50 to 100 nm) that splay and branch as they grow outward, forming spherulites varying from submicron to millimeters in size. The growth of an individual spherulite ceases when it impinges with neighboring spherulites. Only in the theoretical limit of infinite time at the equilibrium melting temperature could a semicrystalline polymer form the thermodynamic ideal single-crystal structure.

Hence, for all practical situations, semicrystalline polymers assume a kinetically-driven, non-equilibrium morphology in the solid state. The overall crystallization kinetics follows the general mathematical formulation that has been developed for the kinetics of phase changes with only minor modifications. The importance of nucleation processes in polymer crystallization has been amply recognized and is based on very general considerations. This concept has been applied to the analysis of the kinetics of polymer crystallization.

Figure 2:
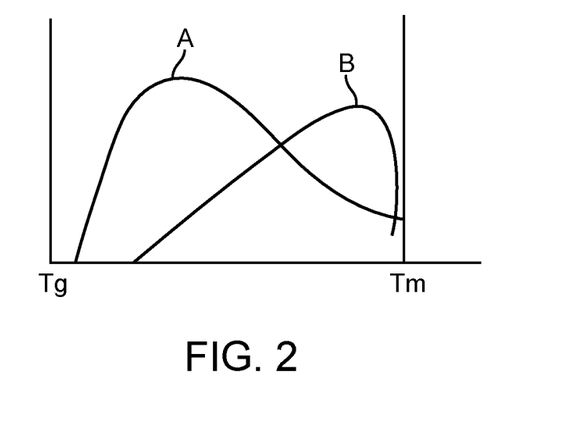
FIG. 2 depicts a schematic plot of the crystal nucleation rate and the crystal growth rate for a polymer.

In general, crystallization tends to occur in a polymer at temperatures between Tg and Tm of the polymer. FIG. 2 shows a schematic of the dependence of nucleation rate (A) and crystal growth rate (B) on temperature between the glass transition temperature (Tg) and the melting temperature (Tm) under quiescent conditions. At temperatures above Tg but far below Tm where polymer chain mobility is limited, nucleation is substantially favored over growth, since the latter process requires much more extensive chain mobility. These nuclei remain present in the polymer until its temperature is elevated above Tm for a period of time. A consequence of the behavior illustrated in FIG. 2 is that at high temperatures there are relatively few, large crystallites formed, while at low temperatures, there are relatively more numerous, smaller crystallites formed.

Various embodiments of the present invention of making a polymeric device can include a step of annealing a polymer construct with no or substantially no crystal growth to increase nucleation density. The method further includes a step of growing crystallites around the formed nuclei after the annealing step. As described in more detail below, the crystallite growth step can be performed by increasing the temperature of the construct, deforming the construct, or both. After the crystal growth step, an implantable medical device, such as a stent, can be fabricated from the polymer construct.

Figures 3A, 3B:
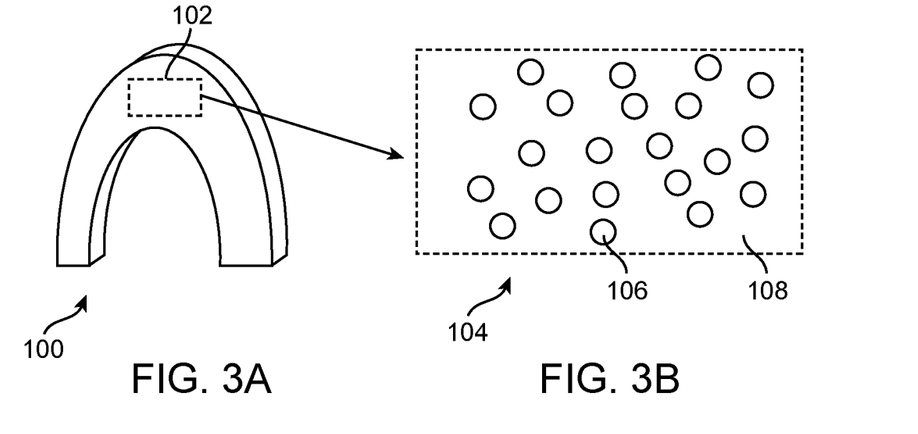
FIG. 3A depicts a strut of a polymeric stent fabricated without annealing.
FIG. 3B is a schematic microstructure of a section of the strut of FIG. 3A.
Figures 4A, 4B:
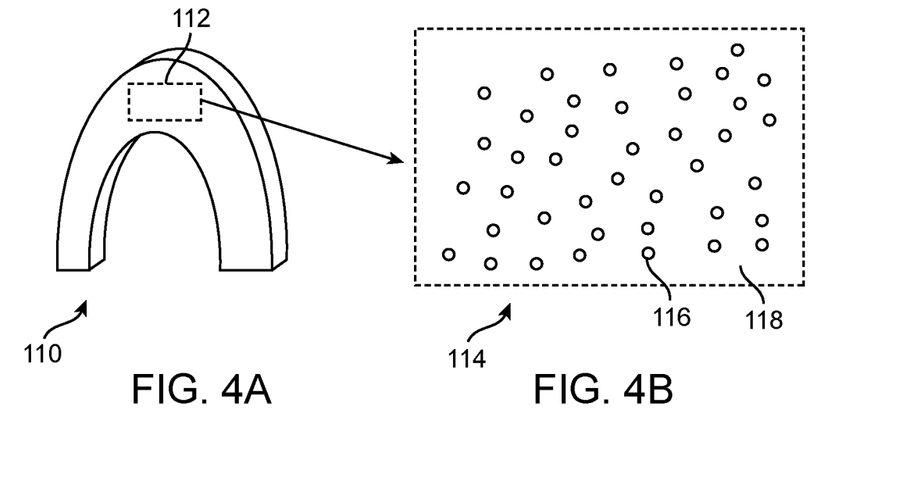
FIG. 4A depicts a strut of a polymeric stent fabricated with annealing.
FIG. 4B is a schematic microstructure of a section of the strut of FIG. 4A.

FIG. 3A depicts a strut 100 of a polymeric stent fabricated without annealing and FIG. 3B is a schematic microstructure 104 of a section 102 of strut 100 showing a small amount of large crystals 106 dispersed within an amorphous region 108. FIG. 4A depicts strut 110 of a polymeric stent fabricated with annealing. FIG. 4B depicts the schematic microstructure 114 of a section 112 of strut 110 showing a large amount of smaller crystals 116 dispersed within an amorphous region 118.

A polymer construct can be a polymer or polymer material formed into a geometrical shape, such as a tube or a sheet. The shape is chosen so that further processing can be applied to form an implantable medical device. For example, a stent pattern can be cut into a tube to form a stent. The polymer construct can be formed using extrusion or injection molding. Alternatively, a polymer tube may be formed from a sheet that is rolled and bonded into a tube.

In such embodiments, the annealing step can include annealing a polymer construct at a temperature or temperature range for a selected annealing time that allows nuclei formation within the polymer with no or substantially no growth of crystallite around the nuclei. The annealing seeds nuclei throughout the polymer construct. The temperature range of annealing can be between Tg and 3, 5, 7, 10, 12, 15 or 18° C. above Tg. Alternatively, the temperature range can be Tg to 0.15×(Tm−Tg).

Exemplary semicrystalline polymers that may be used in embodiments of the present invention include PLLA, poly(D-lactide) (PDLA), polyglycolide (PGA), (poly(L-lactide-co-glycolide) (PLGA), and PLLA-b-poly(ethylene oxide) (PLLA-b-PEO). Literature values of ranges of Tg and Tm of PLLA and PGA are given in Table 1.

TABLE 1

Tg and Tm for PLLA and PGA.

| Polymer | Melting Point (° C.)[1] | Glass Transition Temp (° C.)[1] |
|---------|------------------------|--------------------------------|
| PGA     | 225-230                | 35-40                          |
| PLLA    | 173-178                | 60-65                          |

[1]Medical Plastics and Biomaterials Magazine, March 1998.

The annealing time can be up to 5 min, 10 min, 30 min, 1 hr, or greater than 1 hr. The annealing time can be selected to obtain a desired nucleation density.

As indicated above, after the annealing time, the method further includes a crystal growth step of growing crystallites around the nuclei to obtain a desired crystallinity in the polymer construct. A desired crystallinity may be at least 10%, 10-20%, 20-30%, 30-50%, or greater than 50%. In some embodiments, crystallites can be grown around the formed nuclei by increasing the temperature of the construct to a temperature below Tm that allows crystallite growth. Crystallites can be allowed to grow for a selected crystallite growth time at the increased temperature. Additional nuclei can form and crystallites can grow around the additional nuclei at the increased temperature. The temperature range for crystallite growth can be any temperature between Tg and Tm that allows crystallite growth during a selected time period such as up to 1 min, 10 min, 30 min, 1 hr, or greater than 1 hr. For example, the temperature range can be at least Tg+Z×(Tm−Tg), where Z is 0.1, 0.2-0.4, 0.4-0.8, or 0.8-1.

After the crystallite growth step, the construct can then be subjected to further processing steps in the device fabrication process. For example, a stent pattern can be cut into the tube. Alternatively, the polymer tube can be deformed to increase the strength (as described below) prior to cutting the pattern.

As indicated above, it may be desirable to include a deformation step in the manufacturing process of an implantable medical device to increase the strength along the direction of deformation. Such a deformation step can also grow crystallites around nuclei formed during the annealing step. Thus, in some embodiments, the polymer construct is deformed after the selected annealing time. In such embodiments, the deformation causes crystalline growth around the formed nuclei. In particular, a tubular polymer construct can be radially deformed using known methods such as blow molding, that is described below.

In certain embodiments, the temperature of the polymer construct during deformation can be higher than the annealing temperature range, but lower than Tm. In such embodiments, growth of crystallites can be due to both the deformation and the increase in temperature. The temperature range of the polymer construct during deformation can be Tg+Y× (Tm−Tg), where Y can be 0.1-0.2, 0.2-0.4, or 0.4-0.8.

In other embodiments, the temperature of the polymer construct during deformation can be the same as the temperature during the annealing step. The deformation process can induce growth of crystallites around the nuclei formed during the annealing step. Growth of crystallites during deformation can occur even at temperatures at which there is little or no crystallite growth at quiescent conditions. As stated above, the schematic curve (B) for the crystal growth rate in FIG. 2 corresponds to quiescent conditions, and, thus, does not apply to the crystallite growth during deformation. The temperature of the polymer construct is desirably above Tg during deformation since as described below, Tg represents a transition from a vitreous state to a solid deformable or ductile state. Therefore, a temperature above Tg facilitates deformation of the polymer.

In still further embodiments, a temperature induced crystallite growth step and a deformation step can be performed sequentially. For example, the temperature can be increased to grow crystallites, followed by a deformation step at a selected temperature. Alternatively, a deformation step can be performed, followed by equilibrating the deformed construct at an increased temperature that allows crystallites to grow.

Heating and maintaining a temperature of a polymer construct at an annealing temperature or a crystallite growth temperature can be performed by various methods. For example, the construct in can be heated in a vacuum oven. Alternatively, a warm gas such as nitrogen, oxygen, air, argon, or other gas can be blown on the construct. The temperature of the construct can be maintained by known control methods.

Figure 5:
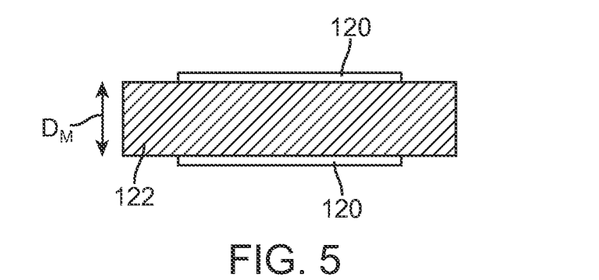
FIG. 5 depicts an axial cross-section of a polymer tube disposed over a mandrel with an inner diameter of the tube the same or substantially the same as an outer diameter of the mandrel.

A polymer construct may have a tendency to change shape upon heating. In particular a polymeric tube may tend to reduce in diameter or shrink upon heating. In some embodiments, the reduction in diameter of a polymer tube during the annealing step or temperature-induced crystal growth steps can be reduced or prevented. Reduction in diameter can be reduced or prevented by disposing a polymeric tube over a mandrel during the heating. The shrinkage of the tube is limited to the outside diameter of the tube. To prevent reduction in diameter, the inside diameter of the tube can be the same or substantially the same as the outside diameter of the mandrel. FIG. 5 illustrates this with an axial cross-section of a polymer tube 120 disposed over a mandrel 122. An inner diameter of tube 120 is the same or substantially the same as an outer diameter Dm of mandrel 122.

Figure 6A:
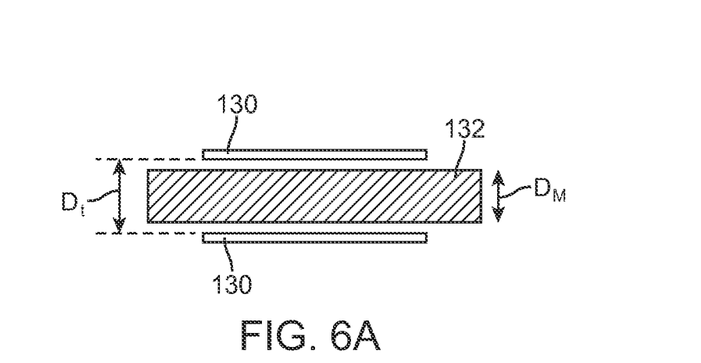
FIG. 6A depicts an axial cross-section of a polymer tube disposed over a mandrel with an inner diameter of the tube greater than an outer diameter of the mandrel.
Figure 6B:
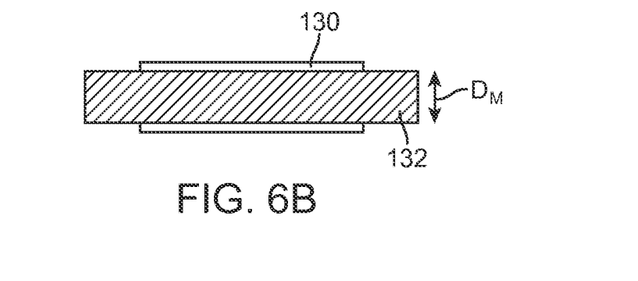
FIG. 6B shows the tube of FIG. 6A tube reduced in diameter due to heating.

To reduce shrinkage, the mandrel has an outside diameter less than the inside diameter of the polymer tube. FIG. 6A depicts this with an axial cross-section of a polymer tube 130 disposed over a mandrel 132. An inner diameter Dt of tube 130 is greater than an outer diameter Dm of mandrel 132. FIG. 6B shows that as tube 130 is heated during annealing or crystallite growth, tube 130 can reduce in diameter, but that the reduction in diameter is limited to the outer diameter Dm of the mandrel.

In further embodiments, shrinkage can be reduced or prevented by maintaining an increased pressure within the tube. For example, the polymer tube can be disposed in a mold, e.g., glass, and the internal pressure is increased during heating by blowing a gas in the tube.

Figure 7A:
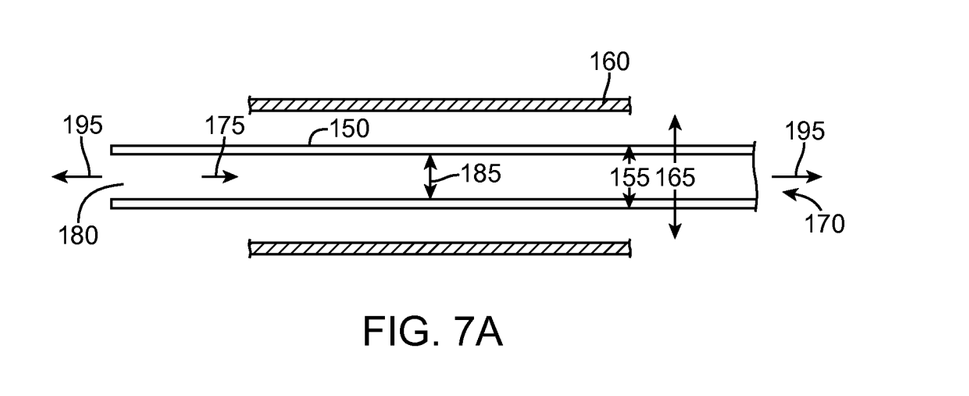
FIG. 7A depicts an axial cross-section of a polymeric tube positioned within a mold.
Figure 7B:
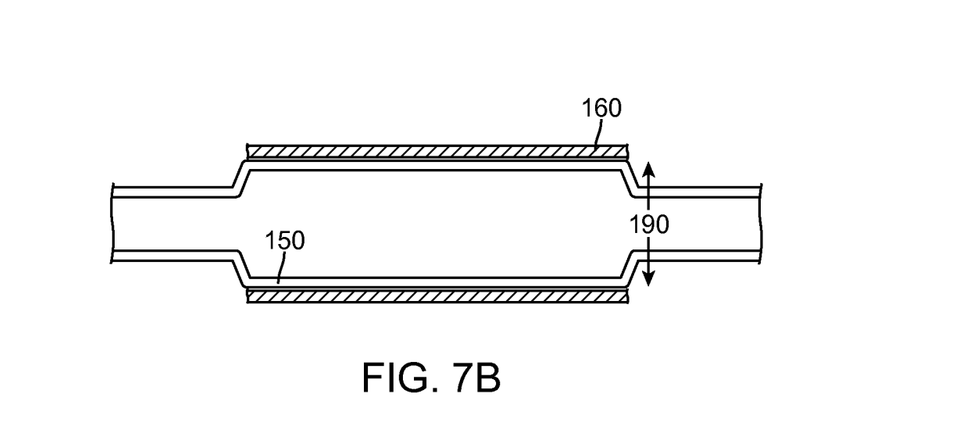
FIG. 7B depicts the polymeric tube of FIG. 7A in a radially deformed state.

As described above, a polymeric tube can be radially deformed using blow molding. FIGS. 7A-B illustrate an embodiment of deforming a polymeric tube using blow molding. FIG. 7A depicts an axial cross-section of a polymeric tube 150 with an outside diameter 155 positioned within a mold 160. Mold 160 limits the radial deformation of polymeric tube 150 to a diameter 165, the inside diameter of mold 160. Polymer tube 150 may be closed at a distal end 170 which may be open in subsequent manufacturing steps. A fluid is conveyed, as indicated by an arrow 175, into an open proximal end 180 of polymeric tube 150. A tensile force 195 can be applied at proximal end 180 and a distal end 170.

Polymeric tube 150 may be heated by heating the fluid to a temperature above ambient temperature prior to conveying the gas into polymeric tube 150. Alternatively, the polymeric tube may be heated by heating the exterior of mold 160 by blowing a warm gas on the mold. The tube may also be heated by a heating element in the mold. The increase in pressure inside of polymer tube 150 facilitated by the increase in temperature of the polymeric tube causes radial deformation of polymer tube 150, as indicated by an arrow 185. FIG. 7B depicts polymeric tube 150 in a deformed state with an outside diameter 190 within mold 160.

Furthermore, the tube may be expanded to a target diameter. In one embodiment, the target diameter may be the diameter at which a stent pattern is formed by laser machining the tube. The target diameter can also correspond to the diameter of a stent prior to crimping. The degree of radial deformation may be quantified by a blow-up ratio or radial draw ratio:

$$\frac{\text{Outside Diameter of Deformed Tube}}{\text{Original Outside Diameter of Tube}}$$

In some embodiments, the radial draw ratio of a polymeric tube for use in fabricating a stent may be between about 1 and 10, or more narrowly between about 2 and 6. Similarly, the degree of axial deformation may be quantified by an axial draw ratio:

$$\frac{\text{Length of Deformed Tube}}{\text{Original Length of Tube}}$$

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Example

The example set forth below are for illustrative purposes only and are in no way meant to limit the invention. The following example is given to aid in understanding the invention, but it is to be understood that the invention is not limited to the particular example. The Example below is provided by way of illustration only and not by way of limitation. The parameters and data are not to be construed to limit the scope of the embodiments of the invention.

PLLA Stent Preparation by Increasing PLLA Nuclei Through Annealing Before Tubing Expansion Step 1 (Tubing Extrusion):

PLLA material is extruded in a signal extruder at 200° C. and the tubing is quickly quenched in cold water or other cooling medium. The size of the extruded tubing is set at about 0.02" for inside diameter (ID) and 0.06" for outside diameter (OD).

Step 2 (Tubing Annealing):

The extruded tubing is annealed at a temperature between 60 to 75° C. for 30 min to 3 h to create a certain amount of PLLA nuclei.

Step 3 (Tubing Expansion):

The annealed tubing is placed in a glass mold and expanded at about 200° F. to obtain biaxial orientation and higher crystallinity. Its final ID and OD are set at about 0.12" and 0.13", respectively.

Step 4 (Stent Preparation):

A stent is cut from the expanded tubing using a femtosecond laser, crimped down to a small size (0.05") on a balloon catheter, and sterilized by electron beam at a dose of 25 kGy.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:
   obtaining a polymeric tube;
   annealing the polymeric tube at a temperature in a temperature range of above Tg and below Tm of a polymer of the polymeric tube with no crystal growth during a selected annealing time of greater than 1 hr;
   after annealing, processing the polymeric tube to increase the crystallinity to a desired crystallinity level; and
   fabricating a stent from the tube after the processing.

2. The method of claim 1, wherein the polymer of the polymeric tube is selected from the group consisting of PLLA and PGA.

3. The method of claim 1, wherein the processing comprises radially deforming the polymeric tube.

4. The method of claim 1, wherein the processing comprises increasing the temperature of the polymeric tube.

5. The method of claim 1, wherein the desired crystallinity level is between 15 and 50%.

6. The method of claim 1, wherein the polymer of the polymeric tube is PLLA.

7. The method of claim 1, wherein the polymer of the polymeric tube is bioabsorbable.

8. The method of claim 1, wherein the annealing of the polymeric tube is at a temperature in a temperature range of Tg+5° C. to Tg+15° C.

9. A method of making a stent comprising:
   obtaining a polymeric tube;
   annealing the polymeric tube at a temperature in a temperature range with no crystal growth during a selected annealing time;
   wherein the polymer comprises PLLA, the temperature range is 60 to 75 deg C., and the selected annealing time is 30 min to 3 hr;
   after annealing, processing the polymeric tube to increase the crystallinity to a desired crystallinity level; and
   fabricating a stent from the tube after the processing.

10. The method of claim 9, wherein the processing comprises increasing the temperature of the polymeric tube.

11. The method of claim 9, wherein the processing comprises radially deforming the polymeric tube.

12. The method of claim 9, wherein the desired crystallinity level is between 15 and 50%.

* * * * *